US009694060B2

(12) United States Patent
Wong

(10) Patent No.: US 9,694,060 B2
(45) Date of Patent: Jul. 4, 2017

(54) PEPTIDE VACCINES BASED ON THE EGFRVIII SEQUENCE FOR THE TREATMENT OF TUMORS

(71) Applicant: The Board of Trustees of the Leland Stanford Junior University, Palo Alto, CA (US)

(72) Inventor: Albert J. Wong, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/417,752

(22) PCT Filed: Aug. 2, 2013

(86) PCT No.: PCT/US2013/053521
§ 371 (c)(1),
(2) Date: Jan. 27, 2015

(87) PCT Pub. No.: WO2014/022835
PCT Pub. Date: Feb. 6, 2014

(65) Prior Publication Data
US 2015/0216956 A1    Aug. 6, 2015

Related U.S. Application Data

(60) Provisional application No. 61/678,800, filed on Aug. 2, 2012.

(51) Int. Cl.
*A61K 47/48* (2006.01)
*A61K 39/00* (2006.01)
*C07K 7/08* (2006.01)

(52) U.S. Cl.
CPC ...... *A61K 39/0011* (2013.01); *A61K 47/4833* (2013.01); *A61K 47/48284* (2013.01); *C07K 7/08* (2013.01); *A61K 2039/6081* (2013.01)

(58) Field of Classification Search
None
See application file for complete search history.

(56) References Cited

U.S. PATENT DOCUMENTS

| | | | |
|---|---|---|---|
| 4,022,878 A | 5/1977 | Gross | |
| 4,329,281 A | 5/1982 | Christenson et al. | |
| 4,526,716 A | 7/1985 | Stevens | |
| 5,037,645 A | 8/1991 | Strahilevitz | |
| 5,112,606 A | 5/1992 | Shiosaka et al. | |
| 5,212,290 A | 5/1993 | Vogelstein et al. | |
| 5,401,828 A | 3/1995 | Vogelstein et al. | |
| 5,710,010 A | 1/1998 | Vogelstein et al. | |
| 5,814,317 A | 9/1998 | Vogelstein et al. | |
| 5,981,725 A | 11/1999 | Vogelstein et al. | |
| 6,127,126 A | 10/2000 | Vogelstein et al. | |
| 6,224,868 B1 | 5/2001 | Wong et al. | |
| 6,455,498 B1 | 9/2002 | Vogelstein et al. | |
| 6,762,165 B2 | 7/2004 | Olivera et al. | |
| 2007/0274991 A1 | 11/2007 | Way et al. | |
| 2009/0220551 A1 | 9/2009 | Sampson et al. | |
| 2013/0332133 A1* | 12/2013 | Horn | ........................ C12N 9/00 703/11 |

FOREIGN PATENT DOCUMENTS

| WO | 9103489 A1 | 3/1991 |
|---|---|---|
| WO | 2005010151 A2 | 2/2005 |
| WO | 2007132461 A2 | 11/2007 |

OTHER PUBLICATIONS

Holmes (Exp. Opin.Invest. Drugs, 2001, 10(3):511-519).*
Tanaka et al. (1985 Proc. Natl. Acad. Sci USA 82:3400-3404).*
Coleman et al. (Research in Immunology, 1994; 145(1):33-36).*
Abaza et al. (Journal of Protein Chemistry, vol. 11, No. 5, 1992, pp. 433-444).*
Wong et al. (Neuro-Oncology Nov. 2015 17 (Suppl. 5): v121-v122, Abs. No. IMPS-40).*
Moscatello et al., Frequent expression of a mutant epidermal growth factor receptor in multiple human tumors, Cancer Res 1995 55(23):5536-5539.
Wong et al., Structural alterations of the epidermal growth factor receptor gene in human gliomas, PNAS 1992 89(7):2965-2969.
Heimberger and Sampson, The PEPvIII-KLH (CDX-110) vaccine in glioblastoma multiforme patients, Expert Opin Biol Ther 2009 9(8):1087-1098.
Francis et al.,Peptide vaccines based on enhanced immunogenicity of peptide epitopes presented with T-cell determinants or hepatitus B core protein, Methods of Enzymol 1989 178:659-676.
Sad et al., Bypass of carrier-induced epitope-specific suppression using a T-helper epitope, Immunolology 1992 76(4):599-603.
MacLean et al., Immunization of breast cancer patients using a synthetic sialyl-Tn glycoconjugate plus Detox adjuvant, Cancer Immunol Immunother 1993 36:215-222.
Landry et al., Antibody recognition of a conformational epitope in a peptide antigen: Rv-peptide complex of an antibody fragment specific for the mutant EGF receptor EGFRvIII, J Mol Biol 2001 308(5):883-893.
Moscatello et al., A naturally occurring mutant human epidermal growth factor receptor as a target for peptide vaccine immunotherapy of tumors, Cancer Res 1997 57(8):1419-1424.
Heimberger et al., Immunological responses in a patient with glioblastoma multiforme treated with sequential courses of temozolomide and immunotherapy: Case study, Neuro-Oncology 2007 10(98-103).
Sampson et al., An epidermal growth factor receptor variant III— targeted vaccine is safe and immunogenic in patients with glioblastoma multiforme, Molecular Cancer Therapeutics 2009 8(10):2773-2779.

* cited by examiner

*Primary Examiner* — Peter J Reddig
(74) *Attorney, Agent, or Firm* — Pepper Hamilton LLP

(57) ABSTRACT

Peptides and vaccine compositions comprising peptides based upon EGFRvIII and lacking a glycine at the splice junction are disclosed. The vaccines can induce immune responses against EGFRvIII. Methods of inhibiting formation or growth of EGFvIII tumors, methods of inducing regression of EGFvIII tumors, methods of immunizing against EGFvIII tumors and methods of treating a subjects who have EGFvIII tumors are disclosed.

20 Claims, 1 Drawing Sheet

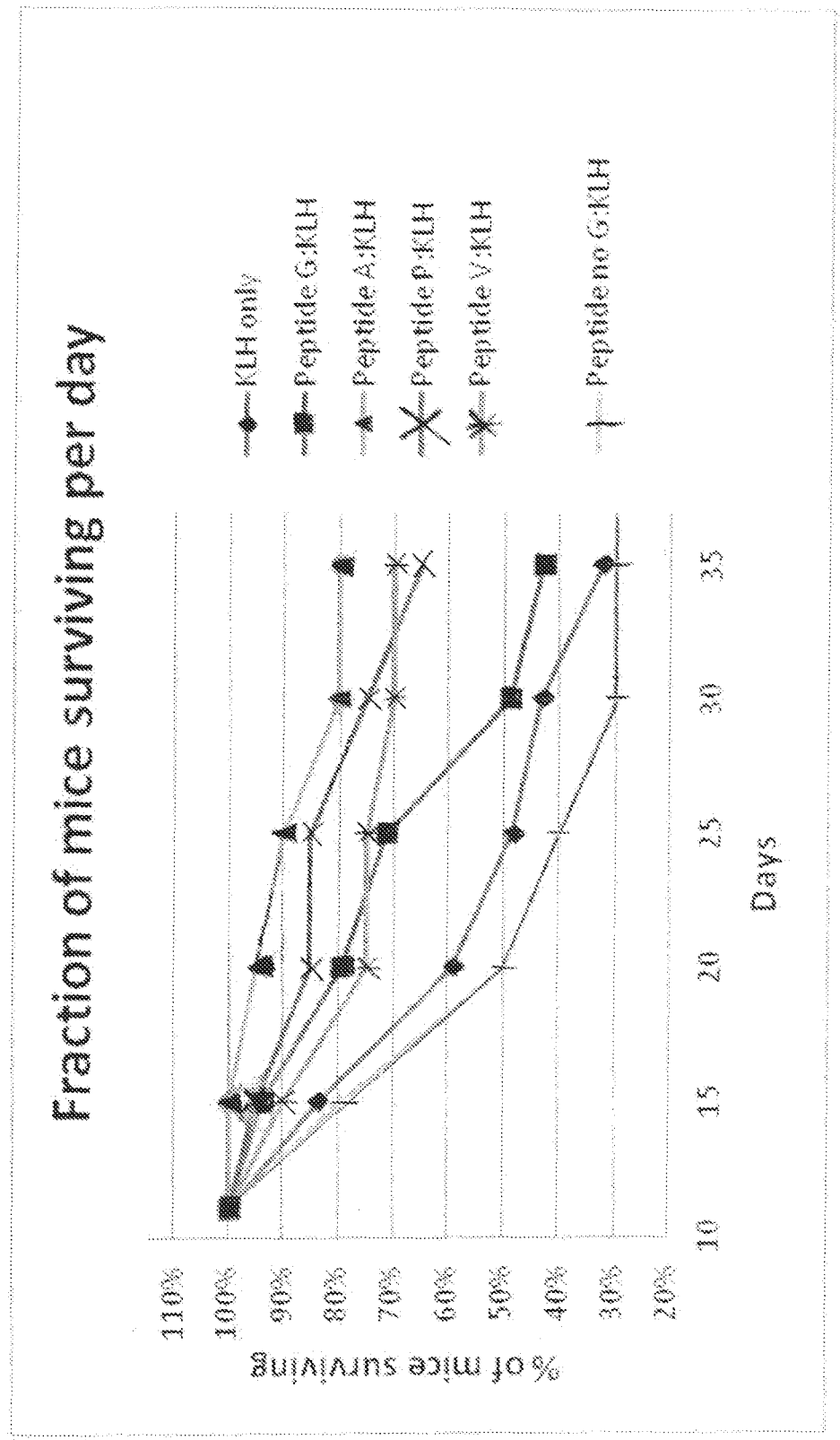

SEQUENCE LISTING

```
<160> NUMBER OF SEQ ID NOS: 22

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 1

Leu Glu Glu Lys Lys Gly Asn Tyr Val Val Thr Asp His
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 2

Leu Glu Glu Lys Lys Gly Asn Tyr Val Val Thr Asp His Cys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 3

Leu Glu Glu Lys Lys Ala Asn Tyr Val Val Thr Asp His
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 4

Leu Glu Glu Lys Lys Val Asn Tyr Val Val Thr Asp His
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 5

Leu Glu Glu Lys Lys Pro Asn Tyr Val Val Thr Asp His
1               5                   10
```

```
<210> SEQ ID NO 6
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 6

Leu Glu Glu Lys Lys Ala Asn Tyr Val Val Thr Asp His Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 7

Leu Glu Glu Lys Lys Val Asn Tyr Val Val Thr Asp His Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 8

Leu Glu Glu Lys Lys Pro Asn Tyr Val Val Thr Asp His Cys
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Asn Tyr Val Val Thr
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 10

Asn Tyr Val Val Thr Asp
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 11

Asn Tyr Val Val Thr Asp His
1               5

<210> SEQ ID NO 12
```

```
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 12

Asn Tyr Val Val Thr Asp His Cys
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 13

Tyr Val Val Thr
1

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 14

Tyr Val Val Thr Asp
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 15

Tyr Val Val Thr Asp His
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 16

Tyr Val Val Thr Asp His Cys
1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 17

Val Val Thr Asp
1

<210> SEQ ID NO 18
<211> LENGTH: 5
```

```
<212> TYPE: PRT
<213> ORGANISM: Artificial Sequence
<220> FEATURE:
<223> OTHER INFORMATION: Synthetic Peptide

<400> SEQUENCE: 18

Val Val Thr Asp His
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 19

Val Val Thr Asp His Cys
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 20

Val Thr Asp His
1

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 21

Val Thr Asp His Cys
1               5

<210> SEQ ID NO 22
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 22

Thr Asp His Cys
1
```

PEPTIDE VACCINES BASED ON THE EGFRVIII SEQUENCE FOR THE TREATMENT OF TUMORS

This application claims priority to U.S. Provisional Application No. 61/678,800 filed Aug. 2, 2012, which is incorporated herein by reference.

GOVERNMENT RIGHTS

This invention was made with Government support under contracts CA124832 and TR001085 awarded by the National Institutes of Health. The Government has certain rights in the invention.

FIELD OF THE INVENTION

The invention relates to peptides useful targets for generating immune responses against cancer cells which express the type III mutant epidermal growth factor receptor. The invention relates to vaccines and methods of using the vaccines in anti-cancer treatments and regimens.

BACKGROUND OF THE INVENTION

Epidermal growth factor receptor (also referred to as EGFR; ErbB-1; and HER1 in humans) is a cell-surface receptor that is activated when it binds to specific ligands, such as epidermal growth factor (EGF) and transforming growth factor α (TGFα). The cDNA sequence corresponding to normal EGF receptor is disclosed in Ullrich et al. Nature 1984 309, 418-425.

Wong et al., Proc Natl Acad Sci USA 1992, 89, 2965-2969 and PCT Application Serial No. PCT/US90/04489 report the genetic alterations associated with rearrangements or deletions of the gene encoding EGFR in five malignant gliomas including the variant EGFR referred to as the Type III mutant EGF receptor (hereinafter EGFRvIII) which is the translation product of a splice variant of the EGFR gene corresponding to a deletion between nucleotides 275-1075 in the EGF receptor cDNA which corresponds to a deletion of the portion of coding sequence encoding the extracellular domain of the receptor corresponding to exons 2 through 7, such that exon 1 is joined to exon 8. The in-frame splice junction formed by the deletion includes a codon that encodes a glycine residue where the two sequences are joined. This glycine residue coding sequence is not found at the corresponding location in either the normal exon 1 coding sequence or the normal exon 8 coding sequence of the normal EGFR gene. The EGFRvIII deletion results in the fusion of what were ordinarily distant sequences to generate a mutated sequence that encodes a novel peptide sequence at this fusion junction.

EGFRvIII is the most frequent, naturally occurring mutant EGFR in human tumors and is particularly prevalent in the brain tumor called glioblastoma multiforme. EGFRvIII has been reported to be present in 56% of glioblastoma tumors and 16% of non-small cell carcinomas of the lung. Moscatello et al. Cancer Res. 1995, 55, 5536-5539 reports that it has also been found to be present in 78% of breast cancers. EGFRvIII was therefore identified as a potentially ideal tumor target because the sequence was not found in any normal tissue.

The deletion corresponding to exons 2 through 7 in which exon 1 is joined to exon 8 is an in frame alteration that creates a codon for a novel glycine at the junction. The amino terminus of the resulting EGFRvIII protein is characterized by the amino acid sequence LEEKKGNYVVTDH, SEQ ID NO:1 where the L represents the first amino acid of the mature protein, and the G is the result of the exon 1 to 8 fusion.

Vaccines comprising peptides corresponding to the EGFRvIII junction have been used to prevent or induce regression of tumors that overexpress EGFRvIII in animal models. The formulation of the vaccine is using the peptide LEEKKGNYVVTDHC SEQ ID NO:2 (in which the terminal cysteine has been added for conjugation purposes) conjugated to immune stimulatory molecule, KLH. The glycine was thought to be a key feature for the recognition of this peptide as foreign by the immune system because it is novel, although without any direct experimental evidence. This particular peptide:KLH conjugate vaccine has now been used in a Phase II clinical trial for glioblastoma where it was shown median survival of 26 months as compared to 15 months for matched historical controls.

Peptides based upon the protein sequence encoded by the splice junction have been described in U.S. Pat. Nos. 6,224,868, 5,212,290, 5,401,828, 5,710,010, 5,814,317, 5,981,725, 6,127,126 and 6,455,498. Additionally, these patents disclose peptides conjugated to carriers such as keyhole limpet hemocyanin (KLH) and their use as vaccines. Sampson et al. US Publication No. 20090220551 discloses EGFRvIII peptides with different C termini and generally discloses methods of using the peptides as adjuvant therapy in cancer treatment protocols.

Heimberger and Sampson, Expert Opin Biol Ther. 2009 August; 9(8): 1087-1098 disclose results from three different clinical trials using an EGFRvIII-KLH conjugate which comprises the EGFRvIII peptide having SEQ ID NO:2 conjugated to KLH to treat patients with glioblastoma. In one trial, patients first had tumors resected followed by radiation therapy. Thereafter, dendritic cells (DCs) were isolated from patients, pulsed with EGFRvIII-KLH conjugate and reintroduced into patients as autologous DCs. In a second trial, patients had tumors resected followed by radiation therapy and then EGFRvIII-KLH conjugate was administered directly to the patients by injection. In the third trial, patients had tumors resected followed by radiation therapy after which EGFRvIII-KLH conjugate was administered directly to the patients by injection while patients underwent chemotherapy using temozolomide (TMZ). In each clinical trial, improvements in time to progress and overall survival were observed compared to historical time to progress and overall survival statistics.

The current vaccine, while showing a significant prolongation in survival, is not curative. Clearly, patients are desirous of treatments that offer the best possible chance at long term survival. As such, there remains a need to provide improved EGFRvIII vaccines to enhance survival. There remains a need for improved compositions and therapies useful to improve clinical outcomes in patients diagnosed with cancer that expresses EGFRvIII.

SUMMARY OF THE INVENTION

The present invention relates to vaccine compositions that comprise a prophylactically or therapeutically effective amount of a peptide conjugated to a carrier, having the formula:

L1-E2-Glu-Lys-Lys-Xaa6-N7-Y8-V9-V10-T11-D12-H13-C14-Carrier wherein
L1 is absent or Leu;
E2 is absent or Glu;
Xaa6 is Ala, Arg, Asn, Asp, Cys, Gln, Glu, His, Ile, Leu, Lys, Met, Phe, Pro, Ser, Thr, Trp, Tyr or Val;

N7 is absent or Asn;
Y8 is absent or Tyr;
V9 is absent or Val;
V10 is absent or Val;
T11 is absent or Thr;
D12 is absent or Asp;
H13 is absent or His;
C14 is Cys or a linking moiety that can link the peptide to Carrier.

In some embodiments, Xaa6 is Ala, Val or Pro. In some embodiments, L1-E2-Glu-Lys-Lys-Xaa6-N7-Y8-V9-V10-T11-D12-H13-C14 comprises at least 4 amino acids, at least 5 amino acids, at least 6 amino acids, at least 7 amino acids, at least 8 amino acids, at least 9 amino acids, at least 10 amino acids, at least 11 amino acids, at least 12 amino acids, at least 13 amino acids or at least 14 amino acids.

In some embodiments, the present invention provides vaccine compositions that comprise a prophylactically or therapeutically effective amount of a peptide conjugated to a carrier, having the formula:

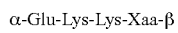

wherein
α is absent, acyl, Leu-Glu; Glu; or Leu;
Xaa is Ala, Arg, Asn, Asp, Cys, Gln, Glu, His, Ile, Leu, Lys, Met, Phe, Pro, Ser, Thr, Trp, Tyr or Val; and
β is absent, Asn, Asn-Tyr, Asn-Tyr-Val, Asn-Tyr-Val-Val, Asn-Tyr-Val-Val-Thr (SEQ ID NO:9), Asn-Tyr-Val-Val-Thr-Asp (SEQ ID NO:10), Asn-Tyr-Val-Val-Thr-Asp-His (SEQ ID NO:11), Asn-Tyr-Val-Val-Thr-Asp-His-Cys (SEQ ID NO:12); Tyr, Tyr-Val, Tyr-Val-Val, Tyr-Val-Val-Thr (SEQ ID NO:13), Tyr-Val-Val-Thr-Asp (SEQ ID NO:14), Tyr-Val-Val-Thr-Asp-His (SEQ ID NO:15), Tyr-Val-Val-Thr-Asp-His-Cys (SEQ ID NO:16), Val, Val-Val, Val-Val-Thr, Val-Val-Thr-Asp (SEQ ID NO:17), Val-Val-Thr-Asp-His (SEQ ID NO:18), Val-Val-Thr-Asp-His-Cys (SEQ ID NO:19), Val-Thr, Val-Thr-Asp, Val-Thr-Asp-His (SEQ ID NO:20), Val-Thr-Asp-His-Cys (SEQ ID NO:21), Thr, Thr-Asp, Thr-Asp-His, or Thr-Asp-His-Cys (SEQ ID NO:22), Asp, Asp-His, Asp-His-Cys, His, His-Cys, or Cys.

In some embodiments, the present invention provides a vaccine composition that comprise a prophylactically or therapeutically effective amount of a peptide conjugated to a carrier in which the peptide has the amino acid sequence selected from the group consisting of: SEQ ID NO:6 (Peptide A), SEQ ID NO:7 (Peptide V), and SEQ ID NO:8 (Peptide P).

In some embodiments, the present invention provides a vaccine composition that comprises a prophylactically or therapeutically effective amount of a peptide conjugated to a carrier is selected from the group consisting of: SEQ ID NO: 6 conjugated to KLH, SEQ ID NO:7 conjugated to KLH, and SEQ ID NO:8 conjugated to KLH.

The present invention further comprises methods of inhibiting formation or growth of tumors bearing a naturally occurring Type III mutant EGF receptor in a human subject. The methods comprise administering to the subject a vaccine provided herein.

The present invention further comprises methods of inducing regression of an existing tumor bearing a naturally occurring Type III mutant EGF receptor in a human subject. The methods comprise administering to the subject a vaccine provided herein.

The present invention further comprises methods of immunizing a human subject who has been identified as being at an elevated risk for developing a tumor comprising tumor cells expressing type III mutant EGF receptors against tumors bearing type III mutant EGF receptors. The methods comprise administering to the subject a vaccine provided herein.

The present invention further comprises methods of treating a human subject who has one or more tumors bearing type III mutant EGF receptors. In some embodiments, the methods comprise the steps of removing at least one tumor bearing type III mutant EGF receptors and/or administering a therapeutically effective amount of radiation and/or administering a therapeutically effective amount of one or more anticancer chemotherapeutics, and additionally administering to the subject a vaccine provided herein. In some embodiments, the methods comprise the steps of tumor is not removed prior to administering a therapeutically effective amount of radiation and/or administering a therapeutically effective amount of one or more anticancer chemotherapeutics, and additionally administering to the subject a vaccine provided herein.

The present invention also provides isolated peptides used in the vaccine provided herein.

BRIEF DESCRIPTION OF THE FIGURE

The FIGURE shows survival over time data from experiments discussed in Example 1.

DETAILED DESCRIPTION OF THE INVENTION

Vaccines which comprise a peptide sequence similar to the fusion junction of EGFRvIII including a substitution of the glycine residue formed at the splice junction of the EGFRvIII receptor are provided. The peptides used in the vaccine are sufficiently similar to EGFRvIII such that an immune response generated against the peptides cross-reacts to EGFRvIII expressed on cancer cells. Generally, the peptides contain portions similar to each of the sequences from the two formerly distant portions of the normal EGF receptor.

It is preferred that the vaccine comprises a peptide conjugated to a hapten/carrier such as keyhole limpet hemocyanin (KLH), bovine serum albumin (BSA) or human serum albumin (HAS).

In some embodiments, the vaccines comprise a peptide selected from the group consisting of LEEKKANYVVTDH (SEQ ID NO:3), LEEKKVNYVVTDH (SEQ ID NO:4), and LEEKKPNYVVTDH (SEQ ID NO:5). In some embodiments, peptides comprise a C-terminal cysteine. In some embodiments, the vaccines comprise a peptide selected from the group consisting of LEEKKANYVVTDHC (SEQ ID NO:6), LEEKKVNYVVTDHC (SEQ ID NO:7), and LEEKKPNYVVTDHC (SEQ ID NO:8). In some embodiments, the vaccines comprise a peptide linked to KLH and are selected from the group consisting of: LEEKKANYVVTDHC:KLH (SEQ ID NO:6 conjugated to keyhole limpet hemocyanin), LEEKKVNYVVTDHC:KLH (SEQ ID NO:7 conjugated to keyhole limpet hemocyanin), and LEEKKPNYVVTDHC:KLH (SEQ ID NO:8 conjugated to keyhole limpet hemocyanin)

Other peptides based upon the EGFRvIII sequence with substitutions of the splice junction glycine may also be used in the vaccines and methods. In some embodiments, peptides, which are optionally linked to a carrier such as for example KLH, BSA or HAS, have the formula:

α-Glu-Lys-Lys-Xaa-β     Formula I wherein
α is absent, acyl, Leu-Glu; Glu; or Leu;
Xaa is Ala, Arg, Asn, Asp, Cys, Gln, Glu, His, Ile, Leu, Lys, Met, Phe, Pro, Ser, Thr, Trp, Tyr or Val; and
β is absent, Asn, Asn-Tyr, Asn-Tyr-Val, Asn-Tyr-Val-Val, Asn-Tyr-Val-Val-Thr (SEQ ID NO:9), Asn-Tyr-Val-Val-Thr-Asp (SEQ ID NO:10), Asn-Tyr-Val-Val-Thr-Asp-His (SEQ ID NO:11), Asn-Tyr-Val-Val-Thr-Asp-His-Cys (SEQ ID NO:12); Tyr, Tyr-Val, Tyr-Val-Val, Tyr-Val-Val-Thr (SEQ ID NO:13), Tyr-Val-Val-Thr-Asp (SEQ ID NO:14), Tyr-Val-Val-Thr-Asp-His (SEQ ID NO:15), Tyr-Val-Val-Thr-Asp-His-Cys (SEQ ID NO:16), Val, Val-Val, Val-Val-Thr, Val-Val-Thr-Asp (SEQ ID NO:17), Val-Val-Thr-Asp-His (SEQ ID NO:18), Val-Val-Thr-Asp-His-Cys (SEQ ID NO:19), Val-Thr, Val-Thr-Asp, Val-Thr-Asp-His (SEQ ID NO:20), Val-Thr-Asp-His-Cys (SEQ ID NO:21), Thr, Thr-Asp, Thr-Asp-His, or Thr-Asp-His-Cys (SEQ ID NO:22), Asp, Asp-His, Asp-His-Cys, His, His-Cys, or Cys. In some embodiments a carrier is optionally linked to a terminal residue such as Cys and if present the carrier is preferably a hapten. In some embodiments, the carrier is KLH, BSA or HSA.

In some embodiments, the vaccines comprise compounds which are optionally linked to a carrier such as for example KLH, BSA or HAS and have the formula:

L1-E2-Glu-Lys-Lys-Xaa6-A7-Y8-V9-V10-T11-D12-H13-C14-Carrier   Formula II;

wherein
L1 is absent or Leu;
E2 is absent or Glu;
Xaa6 is Ala, Arg, Asn, Asp, Cys, Gln, Glu, His, Ile, Leu, Lys, Met, Phe, Pro, Ser, Thr, Trp, Tyr or Val;
N7 is absent or Asn;
Y8 is absent or Tyr;
V9 is absent or Val;
V10 is absent or Val;
T11 is absent or Thr;
D12 is absent or Asp;
H13 is absent or His;
C14 is Cys or a linking moiety that can link the peptide to Carrier; and
Carrier is optional and if present is preferably a hapten. In some embodiments, the carrier is KLH, BSA or HSA.

In some embodiments the peptide of the vaccine has Formula II wherein L1-E2-Glu-Lys-Lys-Xaa6-N7-Y8-V9-V10-T11-D12-H13-C14 and the vaccine comprises at least 4 amino acids, at least 5 amino acids, at least 6 amino acids, at least 7 amino acids, at least 8 amino acids, at least 9 amino acids, at least 10 amino acids, at least 11 amino acids, at least 12 amino acids, at least 13 amino acids or at least 14 amino acids.

In some embodiments, two or more of L1, E2, N7, Y8, V9, V10, T11, D12, H13 and C14 are absent. In some embodiments, L1 and E2 are absent. In some embodiments, L1 and N7 are absent. In some embodiments, L1 and Y8 are absent. In some embodiments, L1 and V9 are absent. In some embodiments, L1 and V10 are absent. In some embodiments, L1 and T11 are absent. In some embodiments, L1 and D12 are absent. In some embodiments, L1 and H13 are absent. In some embodiments, L1 and C14 are absent. In some embodiments, E2 and N7 are absent. In some embodiments, E2 and Y8 are absent. In some embodiments, E2 and V9 are absent. In some embodiments, E2 and V10 are absent. In some embodiments, E2 and T11 are absent. In some embodiments, E2 and D12 are absent. In some embodiments, E2 and H13 are absent. In some embodiments, E2 and C14 are absent. In some embodiments, N7 and Y8 are absent. In some embodiments, N7 and V9 are absent. In some embodiments, N7 and V10 are absent. In some embodiments, N7 and T11 are absent. In some embodiments, N7 and D12 are absent. In some embodiments, N7 and H13 are absent. In some embodiments, N7 and C14 are absent. In some embodiments, Y8 and V9 are absent. In some embodiments, Y8 and V10 are absent. In some embodiments, Y8 and T11 are absent. In some embodiments, Y8 and D12 are absent. In some embodiments, Y8 and H13 are absent. In some embodiments, Y8 and C14 are absent. In some embodiments, V9 and V10 are absent. In some embodiments, V9 and T11 are absent. In some embodiments, V9 and D12 are absent. In some embodiments, V9 and H13 are absent. In some embodiments, V9 and C14 are absent. In some embodiments, V10 and T11 are absent. In some embodiments, V10 and D12 are absent. In some embodiments, V10 and H13 are absent. In some embodiments, V10 and C14 are absent. In some embodiments, T11 and D12 are absent. In some embodiments, T11 and H13 are absent. In some embodiments, T11 and C14 are absent. In some embodiments, D12 and H13 are absent. In some embodiments, D12 and C14 are absent. In some embodiments, H13 and C14 are absent. In some embodiments, three or more of L1, E2, N7, Y8, V9, V10, T11, D12, H13 and C14 are absent. In some embodiments, four or more of L1, E2, N7, Y8, V9, V10, T11, D12, H13 and C14 are absent. In some embodiments, five or more of L1, E2, N7, Y8, V9, V10, T11, D12, H13 and C14 are absent. In some embodiments, six or more of L1, E2, N7, Y8, V9, V10, T11, D12, H13 and C14 are absent. In some embodiments, seven or more of L1, E2, N7, Y8, V9, V10, T11, D12, H13 and C14 are absent. In some embodiments, eight or more of L1, E2, N7, Y8, V9, V10, T11, D12, H13 and C14 are absent. In some embodiments, nine or more of L1, E2, N7, Y8, V9, V10, T11, D12, H13 and C14 are absent. In some embodiments, each of L1, E2, N7, Y8, V9, V10, T11, D12, H13 and C14 are absent. Xaa may be Ala, Arg, Asn, Asp, Cys, Gln, Glu, His, Ile, Leu, Lys, Met, Phe, Pro, Ser, Thr, Trp, Tyr or Val.

The manufacture of peptides is well known. Automated peptide synthesizers may be employed to produce the peptides using techniques that are well known to those having ordinary skill in the art. One having ordinary skill in the art can generate a nucleic acid molecule that encodes a peptide or a protein comprising a peptide and insert it into an expression vector using standard techniques and readily available starting materials. The cloning and expression of proteins is well known as is their purification using for example immunoaffinity, charge or size exclusion.

In some embodiments, the peptide may be linked to a carrier or haptenized to increase immunogenicity. In some cases, the haptenization is the conjugation of a larger molecular structure to the peptide. Haptenization is well known and can be readily performed. Haptenization methods which may be adapted to be used to prepare haptenized peptides include those described in the following U.S. patents which are each incorporated herein by reference: U.S. Pat. No. 5,037,645 issued Aug. 6, 1991 to Strahilevitz; U.S. Pat. No. 5,112,606 issued May 12, 1992 to Shiosaka et al.; U.S. Pat. No. 4,526,716 issued Jul. 2, 1985 to Stevens; U.S. Pat. No. 4,329,281 issued May 11, 1982 to Christenson et al.; and U.S. Pat. No. 4,022,878 issued May 10, 1977 to Gross. Peptide vaccines and methods of enhancing immunogenicity of peptides which may be adapted to modify peptides are also described in Francis et al. 1989 Methods of Enzymol. 178:659-676, which is incorporated herein by reference. Sad et al. 1992 Immunolology 76:599-603, which is incorporated herein by reference, teaches methods of making immunotherapeutic vaccines by conjugating gonadotropin releasing hormone to diphtheria toxoid. Peptides may be similarly conjugated to produce an immunotherapeutic vaccine of the present invention. MacLean et al. 1993 Cancer Immunol. Immunother. 36:215-22.2, which is incorporated herein by reference, describes conjugation methodologies for producing immunotherapeutic vaccines which may be adaptable to produce an immunotherapeutic vaccine of the present invention. The hapten is keyhole limpet hemocyanin which may be conjugated to a peptide.

Pharmaceutical formulations comprising peptides and conjugated peptides may be routinely formulated by one having ordinary skill in the art. Suitable pharmaceutical formulations and components are described in Remington's Pharmaceutical Sciences, A. Osol, a standard reference text in this field, which is incorporated herein by reference. In some embodiments, for example, the vaccine can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). An injectable composition may comprise the peptide or conjugated peptide in a diluting agent such as, for example, sterile water, electrolytes/dextrose, fatty oils of vegetable origin, fatty esters, or polyols, such as propylene glycol and polyethylene glycol.

The vaccines may also comprise an adjuvant. Adjuvants useful in vaccine are well known to those of skill in the art, thus, selection of an appropriate adjuvant can be performed routinely by one of skill in the art upon this disclosure. Examples of useful adjuvant include, but are not limited to, complete and incomplete Freund's, mineral gels such as aluminum hydroxide, surface active substances such as lysolecithin, pluronic polyols, polyanions, peptides and oil emulsions.

In some embodiments, the vaccine is an injectable composition that is sterile, pyrogen free, formulated to be isotonic and free of particulates. The standards of purity required for injectable compositions are well known as are the production and purification methods used to prepare injectable compositions.

The vaccines may be administered by any means that enables the immunogenic agent to be presented to the body's immune system for recognition and induction of an immunogenic response. Pharmaceutical injectable compositions may be administered parenterally, i.e., intravenous, subcutaneous, intramuscular. In some embodiments, pharmaceutical vaccine compositions may be administered intranasally or to tissue in the oral cavity such as by administration sublingually or to buccal tissue.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. An amount of immunogen is delivered to induce a protective or therapeutically effective immune response. Those having ordinary skill in the art can readily determine the range and optimal dosage by routine methods.

The vaccines can be used to treat or prevent tumors that express EGFRvIII. Examples of tumor types that are known to express EGFRvIII include but are not limited to glioblastoma, pediatric brain tumors, non-small cell carcinoma of the lung, ovarian tumors, prostate tumors, head and neck cancers, and breast tumors among several others. In some embodiments, EGFRvIII expression may be confirmed prior to treatment by in vitro detection of EGFRvIII expression in patient samples, in vitro evaluation of patient samples including tumor sample or other samples containing tumor cells, in vivo imaging or detection of EGFRvIII expression or other means to indicate that the patient's cancer expresses EGFRvIII.

In some embodiments, treatment with vaccines is part of a comprehensive treatment protocol which includes surgical resection and/or radiation therapy and/or chemotherapy with anti-cancer compounds, antibodies and the like. In some embodiments, vaccines are administered following resection. In some embodiments, vaccines are administered following radiation therapy. In some embodiments, vaccines are administered together with chemotherapy. In some embodiments, vaccines are administered together with chemotherapy using temozolomide. In some embodiments, vaccines are administered together with chemotherapy using anti-EGFR antibodies.

In some embodiments, vaccines are delivered ex vivo to cells which are then administered to the individual. In some embodiment, the vaccines are delivered as part of an autologous cell therapy protocol whereby cells removed from an individual as treated ex vivo with vaccine and reintroduced in the individual. Dendritic cells and other immune cells may be treated ex vivo and used in cell therapy/vaccine protocols.

The vaccines can be used as antigen targets for producing antibodies including monoclonal antibodies, using any technique which provides for the production of antibodies by continuous cell line in culture. Such techniques are well known to those of skill in the art and include, but are not limited to, the hybridoma technology originally described by Kohler and Milstein, Nature 1975, 256, 495-497, the human B-cell hybridoma technique described by Kosbor et al., Immunology Today 1983, 4, 72 and the EBV-hybridoma technique described by Cole et al., Monoclonal Antibodies and Cancer Therapy, Alan R. Liss, Inc., pp 77-96. Antibodies, including monoclonal antibodies, humanized antibodies, and human antibodies can be prepared and used as therapeutics.

The following nonlimiting examples are provided to further illustrate the invention.

EXAMPLES

Example 1

Studies were undertaken to improve the anti-tumor efficacy of the EGFRvIII vaccine. Vaccines comprising EGFRvIII peptide variations produced and tested show greatly increased tumor regression following vaccination. These EGFRvIII peptide variations included substitutions in the splice junction glycine.

A structural study of the EGFRvIII peptide bound to a single chain recombinant antibody revealed that the novel glycine makes no contacts with the antibody (Landry et al J Mol Biol. 2001; 308(5):883-93). Thus, this glycine may not be essential for immune recognition. However, the glycine might be important for the flexibility of the peptide as the structure of this peptide makes a turn at this amino acid.

Since the glycine was not essential for immune recognition but might contribute to structure, peptides vaccines were prepared with amino acid substitutions for the glycine to determine if such modification enhance the anti-tumor effects of the peptide vaccine. The peptides tested were:

Peptide A
(SEQ ID NO: 6)
LEEKKANYVVTDHC

Peptide V
(SEQ ID NO: 7)
LEEKKVNYVVTDHC

Peptide P
(SEQ ID NO: 8)
LEEKKPNYVVTDHC.

Peptide no G
(SEQ ID NO: 9)
LEEKKNYVVTDHC.

Peptide G
(SEQ ID NO: 2)
LEEKKGNYVVTDHC.

The peptides were conjugated to KLH to produce the following conjugated peptide vaccines.
Peptide A:KLH
Peptide V:KLH
Peptide P:KLH
Peptide no G:KLH
Peptide G:KLH The conjugated peptide vaccines were tested in tumor regression experiments and survival results were compared among animals treating with one of the conjugated peptide vaccines or KLH only. The data is shown in Table 1. Peptide A:KLH, Peptide V:KLH, and Peptide P:KLH each showed better survival rates than those observed with the original conjugated peptide vaccine Peptide G:KLH. Peptide no G:KLH was less effective than Peptide G:KLH which was only slightly more effective than KLH only.

TABLE 1

| Conjugated vaccine | Survival |
|---|---|
| Peptide A: KLH | 90% |
| Peptide V: KLH | 70% |
| Peptide P: KLH | 70% |
| Peptide no G: KLH | 30% |
| Peptide G: KLH | 55% |
| KLH only | 47% |

These vaccines appear to be faster acting, i.e., induce tumor regression in a shorter period of time. They also appear to be more effective, i.e., more animals showed regression using vaccines having G substitutions than with Peptide G:KLH. Thus the data indicate that the central glycine, thought to be essential for activity, can be modified to give superior vaccines.

Additional experiments were performed repeating the experiments described above. Following completion of additional experiments the data was compiled and set forth in Table 2, which shows the overall survival data and total number of animals. Survival over time is shown in the FIGURE. In the overall survival data, use of each of Peptide A:KLH, Peptide V:KLH and Peptide P:KLH resulted in a higher percent survival compared to the use of Peptide G:KLH and Peptide G:KLH was moderately more effective than KLH only.

TABLE 2

| Conjugated vaccine | Survival | Total # of animals |
|---|---|---|
| Peptide A: KLH | 80% | 20 |
| Peptide V: KLH | 70% | 20 |
| Peptide P: KLH | 65% | 20 |
| Peptide no G: KLH | 30% | 10 |
| Peptide G: KLH | 43% | 49 |
| KLH only | 32% | 37 |

For all experiments, the peptides were synthesized with the sequence as indicated with the cysteine at the carboxy terminus added for the purposes of conjugation. Peptides were then conjugated at a 1:1 w/w ratio to maleimide activated Keyhole Limpet Hemocyanin (KLH) for 24 hours. Following conjugation, the peptide:KLH conjugate was dialyzed against PBS to remove unconjugated peptide NIH Swiss mice were inoculated subcutaneously in the right hand flank with $2\times10^6$ HC2 20d2/c cells, an NIH-3T3 cell line engineered to overexpress EGFRvIII. This cell line has been previously used to study anti-tumor responses to SEQ ID NO:2 conjugated to KLH (Moscatello et al., Cancer Res. 57:1419). On the $7^{th}$ day following inoculation, mice were immunized with 100 µg of conjugated peptide in 100 µl of PBS emulsified with 100 µl of Freund's complete adjuvant. On the $14^{th}$ day, mice were immunized with 100 µg of peptide in 100 µl of PBS emulsified with 100 µl of Freund's incomplete adjuvant.

Example 2

Newly diagnosed GBM preferably undergo at least a 95% resection of the T1-gadolinium enhancing component of the tumor. Prior to vaccination all patients preferably receive at least standard of care external beam radiation.

Vaccine administered directly to patients by treating autologous dendritic cells (DCs) ex vivo with vaccine and then reintroducing the vaccinated DCs into the patient. In some embodiments, vaccines is Peptide A:KLH, Peptide V:KLH, or Peptide P:KLH. Vaccine may be loaded onto autologous DCs, which are matured and used for immunization. Patients undergo leukapheresis to obtain peripheral blood mononuclear cells in preparation for DC generation. DCs are pulsed for two hours with 500 µg of vaccine. Patients receive vaccination using autologous vaccinated DCs administered intradermally for examples into the upper thigh, 10 cm below the inguinal ligament, every 2 weeks beginning 2 weeks following completion of radiation therapy. In some embodiments, patients may receive about $3\times10^7$ DCs per injection.

Vaccine may be administered directly to patients. In some embodiments, vaccines is Peptide A:KLH, Peptide V:KLH, or Peptide P:KLH. Newly diagnosed EGFRvIII-positive GBM patients may be treated with vaccine administered given intradermally in GM-CSF without accompanying DCs. In some embodiments, two weeks after completing standard external beam radiation therapy, patients receive 3 vaccinations at 2 week intervals of 500 µg of vaccine in 0.8 mL of saline with GM-CSF. Subsequent vaccines may be continued monthly.

Vaccine may be administered directly to patients in combination with chemotherapy. In some embodiments, the vaccine is Peptide A:KLH, Peptide V:KLH, or Peptide P:KLH. The vaccine may be given in coordination with concurrent daily temozolomide (TMZ) in monthly cycles after completion of radiation. Prior to receiving the vaccine, patients undergo >95% volumetric tumor resection, along with standard of care radiation therapy with concurrent TMZ. Newly diagnosed EGFRvIII-positive GBM patients may be treated with vaccine given intradermally in GM-CSF. Vaccine may be administered in a 500 µg dose with GM-CSF near the inguinal region in the upper thigh, on alternating sides. Patients receive TMZ at a dose of 200 mg/m$^2$ for 5 days of a 28 day cycle or at a dose of 100 mg/m$^2$ for 21 days of a 28 day cycle. In some embodiments, patients are vaccinated on day 21 of each cycle until progression. first three vaccines may be given biweekly, followed by monthly injections.

The Specification includes recitation of the Sequence Listing found in ASCII text file name SeqListingTXT.txt, created and submitted to the United States Patent and Trademark Office on Jan. 27, 2015 (4 kilobytes), which is incorporated by reference in its entirety.

The invention claimed is:

1. A vaccine composition comprising a prophylactically or therapeutically effective amount of a peptide conjugated to a carrier, said vaccine having the formula:

L1-E2-Glu-Lys-Lys-Xaa6-N7-Y8-V9-V10-T11-D12-H13-C14-Carrier wherein
L1 is Leu;
E2 is Glu;
Xaa6 is Ala, Asn, Asp, Ile, Leu, Met, Pro, Trp, Tyr or Val;
N7 is Asn;
Y8 is Tyr;
V9 is Val;
V10 is Val;
T11 is Thr;
D12 is Asp;
H13 is His;
C14 is Cys or a linking moiety that can link the peptide to the Carrier; and
the carrier is linked to C14.

2. The vaccine of claim 1 wherein the carrier is a hapten.

3. The vaccine of claim 1 wherein the carrier is KLH, BSA or HSA.

4. The vaccine of claim 1 wherein C14 is Cys.

5. The vaccine of claim 1 wherein Xaa6 is Asn, Asp, Ile, Leu, Met, Trp, or Tyr.

6. A vaccine composition comprising a prophylactically or therapeutically effective amount of a peptide conjugated to a carrier, wherein said peptide conjugated to the carrier is selected from the group consisting of: Peptide A:KLH (SEQ ID NO: 6:KLH), Peptide V:KLH (SEQ ID NO:7:KLH), and Peptide P:KLH (SEQ ID NO:8:KLH).

7. The vaccine of claim 1 wherein said vaccine is a sterile, pyrogen free composition.

8. A method of inhibiting formation or growth of tumors bearing a naturally occurring Type III mutant EGF receptor in a human subject comprising administering to said subject a vaccine of claim 1.

9. A method of inducing regression of an existing tumor bearing a naturally occurring Type III mutant EGF receptor in a human subject comprising administering to said subject a vaccine of claim 1.

10. A method of immunizing a human subject who has been identified as being at an elevated risk for developing a tumor comprising tumor cells expressing type III mutant EGF receptors against tumors bearing type III mutant EGF receptors, comprising: administering to said subject a vaccine of claim 1.

11. A method of treating a human subject who has one or more tumors bearing type III mutant EGF receptors, comprising a) either i) removing at least one tumor bearing type III mutant EGF receptors, and/or ii) administering a therapeutically effective amount of radiation, and/or iii) administering a therapeutically effective amount of one or more anticancer chemotherapeutics, and b) administering to said subject a vaccine of claim 1.

12. The method of claim 11 comprising iii) administering a therapeutically effective amount of one or more anticancer chemotherapeutics selected from the group consisting of temozolomide and anti-EGFR antibodies.

13. The method of claim 11 comprising diagnosing the tumor as expressing type III mutant EGF receptors by detecting EGFRvIII protein or mRNA in a sample removed from said subject.

14. The method of claim 11 wherein said tumor is a glioma.

15. The vaccine of claim 1 wherein the carrier is KLH.

16. The vaccine of claim 4 wherein the carrier is KLH.

17. A method of inhibiting formation or growth of tumors bearing a naturally occurring Type III mutant EGF receptor in a human subject or inducing regression of an existing tumor bearing a naturally occurring Type III mutant EGF receptor in a human subject comprising administering to said subject a vaccine of claim 4.

18. A method of immunizing a human subject who has been identified as being at an elevated risk for developing a tumor comprising tumor cells expressing type III mutant EGF receptors against tumors bearing type III mutant EGF receptors, comprising: administering to said subject a vaccine of claim 4.

19. A method of treating a human subject who has one or more tumors bearing type III mutant EGF receptors, comprising a) either i) removing at least one tumor bearing type III mutant EGF receptors, and/or ii) administering a therapeutically effective amount of radiation, and/or iii) administering a therapeutically effective amount of one or more anticancer chemotherapeutics, and b) administering to said subject a vaccine of claim 4.

20. The method of claim 19 wherein said tumor is a glioma.

\* \* \* \* \*